United States Patent

Schwab et al.

(10) Patent No.: US 6,201,130 B1
(45) Date of Patent: Mar. 13, 2001

(54) N-ARYLSULFONYLAMINO ACID OMEGA-AMIDES

(75) Inventors: Wilfried Schwab, Wiesbaden; Werner Thorwart, Hochheim; Manfred Schudok, Eppstein/Ts.; Burkhard Haase, Hofheim, all of (DE)

(73) Assignee: Aventis Pharma Duetschland GmbH, Frankfurt am Main (DE)

( * ) Notice: Subject to any disclaimer, the term of this patent is extended or adjusted under 35 U.S.C. 154(b) by 0 days.

(21) Appl. No.: 09/434,107

(22) Filed: Nov. 5, 1999

(30) Foreign Application Priority Data

Nov. 6, 1998 (DE) .............................. 198 51 184

(51) Int. Cl.[7] .................. C07D 209/04; A61K 31/403
(52) U.S. Cl. .................. 548/452; 548/454; 548/572; 548/574; 548/575; 514/359; 514/408; 514/410
(58) Field of Search ................... 548/452, 454, 548/572, 574, 575; 514/359, 408, 410

(56) References Cited

FOREIGN PATENT DOCUMENTS

| 0 305 947 | 3/1989 | (EP) . |
|---|---|---|
| 0 606 046 | 7/1994 | (EP) . |
| 0 468 231 | 9/1994 | (EP) . |
| 0 757 037 | 2/1997 | (EP) . |
| 0 877 018 | 11/1998 | (EP) . |
| WO 95/35276 | 12/1995 | (WO) . |
| WO 96/27583 | 9/1996 | (WO) . |
| WO 97/44315 | 11/1997 | (WO) . |

OTHER PUBLICATIONS

K. U. Weithmann et al., "Effects of Tiaprofenic Acid on Urinary Pyridinium Crosslinks in Adjuvant Arthritic Rats: Comparison with Doxycycline", Inflamm. Res. 46 (1997) 246–252.

Qi–Zhang Ye et al., "Purification and Characterization of the Human Stromelysin Catalytic Domain Expressed in *Escherichia coli*", Biochemistry 1992, 31, pp. 11231–11235.

Jatinder P. Bassin et al., "Chlorosulfonation of Some Polynuclear Heterocyclic Compounds", Phosphorus, Sulfur, and Silicon, 1992, vol. 72, pp. 157–170.

Amanda J. Fosang et al., "Aggrecan is Degraded by Matrix Metalloproteinases in Human Arthritis", The American Society for Clinical Investigation, Inc., vol. 98, No. 10, Nov. 1996, pp. 2292–2299.

Anil S. Guram et al., "A Simple Catalytic Method for Synthesis of Arylamines from Aryl Bromides", Angew. Chem. 1995, 107, No. 12, pp. 1456–1459.

Xicai Huang et al., "Controlled Regioselective Anilide Formation from Aspartic and Glutamic Acid Anhydrides", J. Org. Chem. 1997, 62, pp. 8821–8825.

C. M. Suter, "Studies in the Diphenyl Ether Series. II. Preparation and Structure of Some Sulfonic Acids and Related Derivatives", Contribution from the Chemical Laboratory of Northwestern University, Mar. 6, 1931, vol. 53, pp. 1112–1116.

Chem. Abstract WO 9745424, DN 128:61425, Dec. 4, 1997.*

\* cited by examiner

*Primary Examiner*—Alan L. Rotman
*Assistant Examiner*—Rita Desai
(74) *Attorney, Agent, or Firm*—Finnegan, Henderson, Farabow, Garrett, & Dunner, L.L.P.

(57) ABSTRACT

Compounds of the formula I:

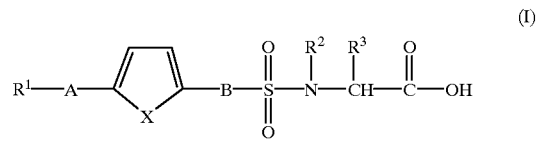

stereoisomeric forms, and physiologically tolerable salts thereof are suitable for the production of pharmaceuticals for the therapy and prophylaxis of disorders involving matrix-degrading metalloproteinases.

6 Claims, No Drawings

N-ARYLSULFONYLAMINO ACID OMEGA-AMIDES

The invention relates to novel N-arylsulfonylamino acid omega-amides, processes for their preparation, and processes for their use as pharmaceuticals.

The publications EP 0 606 046, WO 95/35276 and WO 96/27583 describe arylsulfonaminohydroxamic acids and their action as matrix metalloproteinase inhibitors. Specific arylsulfonamidocarboxylic acids are used as intermediates for the preparation of thrombin inhibitors (EP 0 468 231) and aldose reductase inhibitors (EP 0 305 947). The publication EP 0 757 037 also describes the action of sulfonylamino acid derivatives as metalloproteinase inhibitors.

In the effort to find efficacious compounds for the treatment of connective tissue disorders, it has now been found that the sulfonylaminocarboxylic acids according to the invention are strong inhibitors of matrix metalloproteinases. Particular value is placed here on the inhibition of stromelysin (MMP-3) and neutrophil collagenase (MMP-8), as both enzymes are decisively involved in the degradation of the proteoglycans, as important constituents of the cartilaginous tissue (A. J. Fosang et al. J. Clin. Invest. 98 (1996) 2292–2299). Those enzymes which are involved in the constitutive degradation and synthesis of matrix constituents likewise belong to the protein family of the matrix metalloproteinases. For example, MMP-1 (collagenase-1) has an important vital function, since it is involved in natural collagen degradation, in particular even where morphogenetic changes take place. Medicinal active compounds which, although they are able to inhibit MMP-3 and MMP-8, at the same time leave MMP-1 largely unaffected, are thus preferred. Such an active compound can even be particularly preferred with respect to the healing of the human or animal body, which, with, all in all, only moderate inhibition of MMP-3 and -8, shows no or a weaker effect on the MMP-1.

The invention therefore relates to the compound of the formula I:

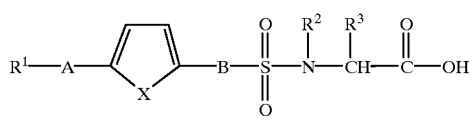

(I)

wherein, $R^1$ is selected from
1) unsubstituted phenyl,
2) phenyl monosubstituted or disubstituted with at least one substituent selected from linear $(C_1–C_6)$-alkyl, branched $(C_1–C_6)$-alkyl, cyclic $(C_3–C_6)$-alkyl, hydroxyl, $(C_1–C_6)$-alkyl-C(O)—O—, $(C_1–C_6)$-alkyl-O—, $(C_1–C_6)$-alkyl-O—$(C_1–C_4)$-alkyl-O—, halogen, $CF_3$, CN, $NO_2$, HO—C(O)—, $(C_1–C_6)$-alkyl—O—C(O)—, methylenedioxo, $R^4$—$(R^5)$N—C(O)—, and $R^4$—$(R^5)$N—; substituted or unsubstituted isoxazolidine, morpholine, isothiazolidine, thiomorpholine, pyrazolidine, imidazolidine, piperazine, azetidine, pyrrole, pyrroline, pyrrolidine, pyridine, azepine, piperidine, oxazole, isoxazole, imidazole, pyrazole, thiazole, isothiazole, diazepine, thiomorpholine, pyrimidine, and pyrazine; and
3) a substituted or unsubstituted heteroaromatic group selected from pyrrole, pyrazole, imidazole, triazole, thiophene, thiazole, oxazole, isoxazole, pyridine, pyrimidine, indole, benzothiophene, benzimidazole, benzoxazole and benzothiazole;

$R^2$ is selected from
1) hydrogen,
2) $(C_1–C_6)$-alkyl,
3) HO—C(O)—$(C_1–C_6)$-alkyl,
4) picolyl; and
5) phenyl-$(CH_2)_n$—, where phenyl is unsubstituted, or monosubstituted or disubstituted with at least one substituent selected from linear $(C_1–C_6)$-alkyl, branched $(C_1–C_6)$-alkyl, cyclic $(C_3–C_6)$-alkyl, hydroxyl, $(C_1–C_6)$-alkyl-C(O)—O—, $(C_1–C_6)$-alkyl-O—, $(C_1–C_6)$-alkyl-O—$(C_1–C_4)$-alkyl-O—, halogen, $CF_3$, CN, $NO_2$, HO—C(O)—, $(C_1–C_6)$-alkyl-O—C(O), methylenedioxo, $R^4$—$(R^5)$NC(O), and $R^4$—$(R^5)$N—;
n is selected from zero, 1, and 2;

$R^4$ and $R^5$ are independently selected from
1) hydrogen,
2) $(C_1–C_6)$-alkyl,
3) HO—C(O)—$(C_1–C_6)$-alkyl,
4) picolyl; and
5) phenyl-$(CH_2)_n$—, where phenyl is unsubstituted, monosubstituted, or disubstituted with at least one substituent selected from linear $(C_1–C_6)$-alkyl, branched $(C_1–C_6)$-alkyl, cyclic $(C_3–C_6)$-alkyl, hydroxyl, $(C_1–C_6)$-alkyl-C(O)—O—, $(C_1–C_6)$-alkyl-O—, $(C_1–C_6)$-alkyl-O—$(C_1–C_4)$-alkyl-O—, halogen, $CF_3$, CN, $NO_2$, HO—C(O)—, $(C_1–C_6)$-alkyl-O—C(O), methylenedioxo, $R^{4a}$—$(R^{5a})$N—C(O), and $R^{4a}$—$(R^{5a})$N—;
where $R^{4a}$ and $R^{5a}$ are independently selected from hydrogen, $(C_1–C_6)$-alkyl, HO—C(O)—$(C_1–C_6)$-alkyl, substituted or unsubstituted phenyl-$(CH_2)_n$—, and picolyl;
n is selected from zero, 1, and 2;
or together $R^4$ and $R^5$, form a 4, 5, 6, or 7 membered ring with the nitrogen to which $R^4$ and $R^5$ are attached wherein at least one of the ring atoms is selected from
1) oxygen,
2) sulfur,
3) NH, and
4) carbon;

$R^3$ is selected from
1) —$(C_1–C_4)$-alkyl-C(O)—N($R^6$)—$R^7$,
2) —$(C_1–C_4)$-alkyl-C(O)—Y, and
3) —$(C_1–C_4)$-alkyl-C(O)—N($R^9$)—$(CH^2)$O—N$(R^4)$—$R^5$;

where $R^6$ and $R^7$ together with the nitrogen to which they are bonded form a radical selected from formulae IIa, IIb, and IIe:

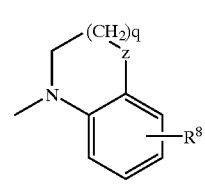

(IIa)

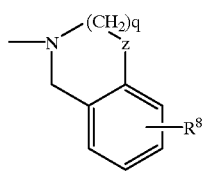
(IIe)

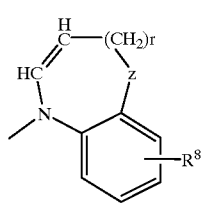
(IIb)

q is selected from zero, 1 and 2, and
r is selected from zero and 1,
Z is selected from
1) carbon,
2) nitrogen,
3) oxygen,
4) sulfur, and
5) a covalent bond;

$R^8$ is selected from
1) hydrogen
2) linear $(C_1-C_6)$-alkyl,
3) branched $(C_1-C_6)$-alkyl,
4) cyclic $(C_3-C_6)$-alkyl,
5) hydroxyl,
6) $(C_1-C_6)$-alkyl-C(O)—O—,
7) $(C_1-C_6)$-alkyl-O—,
8) $(C_1-C_6)$-alkyl-O—$(C_1-C_4)$-alkyl-O—,
9) halogen,
10) $CF_3$,
11) CN,
12) $NO_2$,
13) HO—C(O)—,
14) $(C_1-C_6)$-alkyl-O—C(O)—,
15) methylenedioxo,
16) $R^4$—$(R^5)$N—C(O)—, and
17) $R^4$—$(R^5)$N—,
o is selected from 2, 3, 4, and 5;
Y is selected from formulae IIc and IId:

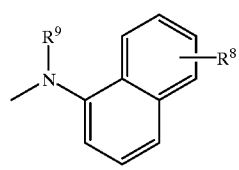
(IIc)

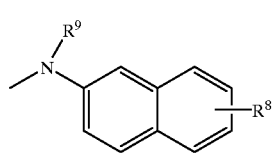
(IId)

$R^9$ is selected from
1) hydrogen,
2) $(C_1-C_6)$-alkyl-,
3) HO—C(O)—$(C_1-C_6)$-alkyl-,
4) picolyl,
5) phenyl-$(CH_2)_n$—, where phenyl is unsubstituted or monosubstituted or disubstituted with at least one substituent selected from linear $(C_1-C_6)$-alkyl, branched $(C_1-C_6)$-alkyl, cyclic $(C_3-C_6)$-alkyl, hydroxyl, $(C_1-C_6)$-alkyl-C(O)—O—, $(C_1-C_6)$-alkyl-O—, $(C_1-C_6)$-alkyl-O—$(C_1-C_4)$-alkyl-O—, halogen, $CF_3$, CN, $NO_2$, HO—C(O)—, $(C_1-C_6)$-alkyl-O—C(O), methylenedioxo, $R^4$—$(R^5)$N—C(O), and $R^4$—$(R^5)$N—;
n is selected from zero, 1, and 2;
A is selected from a covalent bond, —O—, —CH=CH—, and —C≡C—;
B is selected from —$(CH_2)_m$—, —O—$(CH_2)_p$, and —CH=CH—
where m is selected from zero, 1, 2, 3, 4, 5, and 6;
p is selected from 1, 2, 3, 4, and 5;
X is selected from —CH=CH—, oxygen and sulfur;
a stereoisomer or physiologically tolerable salt thereof.

In one embodiment, the invention provides for a compound of formula I, wherein
$R^1$ is selected from
1) unsubstituted phenyl and
2) phenyl monosubstitued with a substituent selected from linear $(C_1-C_6)$-alkyl-, branched $(C_1-C_6)$-alkyl-, cyclic $(C_3-C_6)$-alkyl-, —OH, $(C_1-C_6)$-alkyl-C(O)—O—, $(C_1-C_6)$-alkyl-O—, $(C_1-C_6)$-alkyl-O—$(C_1-C_4)$-alkyl-O—, halogen, —$CF_3$, or $R^4$—$(R^5)$N—;

$R^2$ is selected from hydrogen and $(C_1-C_6)$-alkyl;
$R^4$ and $R^5$ are independently selected from
hydrogen and $(C_1-C_6)$-alkyl-, and
R and $R^5$ together form a 4, 5, 6, or 7 membered ring with the nitrogen to which $R^4$ and $R^5$ are attached, wherein at least one of the ring atoms is selected from oxygen, sulfur, NH, and carbon;

$R^3$ is selected from
1) —$(C_1-C_4)$-alkyl-C(O)—N($R^6$)—$R^7$,
2) —$(C_1-C_4)$-alkyl-C(O)—Y, and
3) —$(C_1-C_4)$-alkyl-C(O)—N($R^9$)—$(CH_2)_o$—N($R^4$)—$R^5$;
$R^6$ and $R^7$ together with the nitrogen to which they are bonded form a radical of formula IIa;
q is selected from zero and 1;
Z is selected from carbon, nitrogen, oxygen, and sulfur;
$R^8$ is selected from hydrogen, linear $(C_1-C_6)$-alkyl, branched $(C_1-C_6)$-alkyl, cyclic $(C_3-C_6)$-alkyl hydroxyl, $(C_1-C_6)$-alkyl-C(O)—O—, $(C_1-C_6)$-alkyl-O—, $(C_1-C_6)$-alkyl-O—$(C_1-C_4)$-alkyl-O—, halogen, $CF_3$, and CN;
$R^9$ is a hydrogen atom;
o is selected from 2 and 3;
A is selected from a covalent bond and —O—;
B is selected from $(CH_2)_m$— and —O—$(CH_2)_p$;
m is selected from 0, 1, and 2;
p is selected from 1 and 2; and
X is —CH=CH—.

In another embodiment of the invention, in the compound of formula I,
$R^1$ is selected from
1) unsubstituted phenyl, and
2) phenyl monosubstituted with a substituent selected from chlorine, bromine, fluorine, pyrrolidine, and morpholine;

$R^2$ is a hydrogen atom;
$R^3$ is selected from
1) —($C_1$–$C_4$)-alkyl-C(O)—N($R^6$)—$R^7$,
2) —($C_1$–$C_4$)-alkyl-C(O)—Y, and
3) —($C_1$–$C_4$)-alkyl-C(O)—N($R^9$)—($CH_2$)o—N($R^4$)—$R^5$;
   q is selected from 0 and 1;
   z is carbon;
   $R^8$ is selected from hydrogen, chlorine, bromine, and flourine;
   $R^9$ is hydrogen;
   o is selected from 2 and 3;
$R^4$ and $R^5$ are independently selected from hydrogen, phenyl, and morpholine;
A is selected from a covalent bond and —O—;
B is a covalent bond; and
X is —CH=CH.

The compounds 2-(biphenyl-4-sulfonylamino)-4-(naphthalen-1-ylcarb-amoyl)butyric acid, 2-(biphenyl-4-sulfonylamino)-4-(naphthalen-2-yl-carbamoyl)butyric acid, 2-(biphenyl-4-sulfonylamino)-4-(2-phenylamino-ethylcarbamoyl)butyric acid, 2-(4'-chloro-biphenyl-4-sulfonylamino)-4-(3-morpholin-4-ylpropylcarbamoyl) butyric acid, 4-(3-(4-(biphenyl-4-sulfonylamino)-4-carboxybutyrylamino)propyl)morpholin-4-ium trifluoroacetate, 2-(biphenyl-4-sulfonylamino)-5-(2,3-dihydroindol-1-yl)-5-oxopentanoic acid, 5-(2,3-dihydroindol-1-yl)-5-oxo-2-(4'-pyrrolidin-1-yl-biphenyl-4-sulfonylamino)pentanoic acid, 2-(4'-chlorobiphenyl-4-sulfonylamino)-5-(2,3-dihydroindol-1-yl)-5-oxopentanoic acid, 2-(4'-bromobiphenyl-4-sulfonylamino)-5-(2,3-dihydroindol-1-yl)-5-oxopentanoic acid, 2-(4'-chloro-biphenyl-4-sulfonylamino)-5-(5-fluoro-2,3-dihydroindol-1-yl)-5-oxopentanoic acid, 2-(4'-bromobiphenyl-4-sulfonylamino)-5-(5-fluoro-2,3-dihydroindol-1-yl)- 5-oxopentanoic acid, 5-(5-fluoro-2,3-dihydroindol-1-yl)-5-oxo-2-(4'-pyrrolidin-1-ylbiphenyl-4-sulfonylamino)pentanoic acid and 5-(5-fluoro-2,3-dihydroindol-1-yl)-2-(4'-morpholin-4-yl-biphenyl-4-sulfonylamino)-5-oxopentanoic acid are currently particularly preferred.

It is understood that the heterocycle substituents of $R^1$; which include isoxazolidine, morpholine, isothiazolidine, thiomorpholine, pyrazolidine, imidazolidine, piperazine, azetidine, pyrrole, pyrroline, pyrrolidine, pyridine, azepine, piperidine, oxazole, isoxazole, imidazole, pyrazole, thiazole, isothiazole, diazepine, thiomorpholine, pyrimidine, and pyrazine; may be substituted with at least one substituent selected from linear ($C_1$–$C_6$)-alkyl, branched ($C_1$–$C_6$)-alkyl, cyclic ($C_3$–$C_6$)-alkyl, hydroxyl, ($C_1$–$C_6$)-alkyl-C(O)—O—, ($C_1$–$C_6$)-alkyl-O—, ($C_1$–$C_6$)-alkyl-O—($C_1$–$C_4$)-alkyl-O—, halogen, $CF_3$, CN, $NO_2$, HO—C(O)—, ($C_1$–$C_6$)-alkyl-O—C(O)—, methylenedioxo, $R^4$—($R^5$) N—C(O)—, and $R^4$—($R^5$)N—.

It is also understood that the heteroaromatic group substituents of $R^1$; which include pyrrole, pyrazole, imidazole, triazole, thiophene, thiazole, oxazole, isoxazole, pyridine, pyrimidine, indole, benzothiophene, benzimidazole, benzoxazole and benzothiazole; may be substituted with at least one substituent selected from linear ($C_1$–$C_6$)-alkyl, branched ($C_1$–$C_6$)-alkyl, cyclic ($C_3$–$C_6$)-alkyl, hydroxyl, ($C_1$–$C_6$)-alkyl-C(O)—O—, ($C_1$–$C_6$)-alkyl-O—, ($C_1$–$C_6$)-alkyl-O—($C_1$–$C_4$)-alkyl-O—, halogen, $CF_3$, CN, $NO_2$, HO—C(O)—, ($C_1$–$C_6$)-alkyl-O—C(O)—, methylenedioxo, $R^4$—($R^5$) N—C(O)—, and $R^4$—($R^5$)N—.

It is further understood that a substituted phenyl includes, but is not limited to, the following substituents: linear ($C_1$–$C_6$)-alkyl, branched ($C_1$–$C_6$)-alkyl, cyclic ($C_3$–$C_6$)-alkyl, hydroxyl, ($C_1$–$C_6$)-alkyl-C(O)—O—, ($C_1$–$C_6$)-alkyl-O—, ($C_1$–$C_6$)-alkyl-O—($C_1$–$C_4$)-alkyl-O—, halogen, $CF_3$, CN, $NO_2$, HO—C(O)—, ($C_1$–$C_6$)-alkyl-O—C(O), and methylenedioxo.

When $R^4$ and $R^5$ together form a 4, 5, 6, or 7 membered ring with the nitrogen to which $R^4$ and $R^5$ are attached wherein at least one of the ring atoms is selected from oxygen, sulfur, NH, and carbon, it is understood that that ring may be derived from compounds including isoxazolidine, morpholine, isothiazolidine, thiomorpholine, pyrazolidine, imidazolidine, piperazine, azetidine, pyrrole, pyrroline, pyrrolidine, pyridine, azepine, piperidine, pyrazole and diazepine.

The term "halogen" is understood as meaning fluorine, chlorine, bromine or iodine.

The term "alkyl" is understood as meaning hydrocarbon radicals whose carbon chain is linear or branched.

The starting substances of the chemical reactions are known or can easily be prepared by methods known from the literature.

The invention furthermore relates to processes for the preparation of the compound of the formula I, a stereoisomeric form thereof, and a physiologically tolerable salt thereof.

In one process, a compound of formula I is prepared by
a) reacting an aminocarboxylic acid of the formula II:

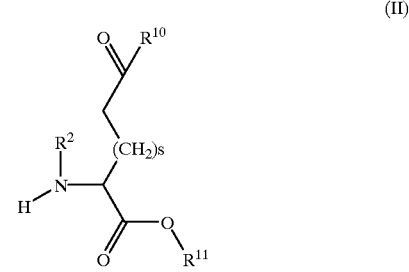

(II)

$R^{11}$ is selected from hydrogen and an ester protecting group;
s is selected from zero, 1, 2 and 3;
$R^{10}$ is selected from —$OR^{12}$, a hydrogen atom, and —N($R^6$)—$R^7$,
$R^{12}$ is an ester protecting group;
with a sulfonic acid derivative of the formula III:

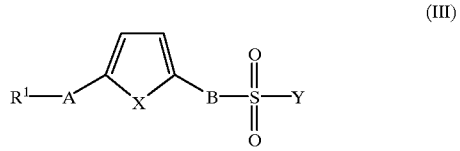

(III)

wherein Y is selected from
1) halogen,
2) imidazolyl, and
3) $OR^{13}$;
   $R^{13}$ is selected from substituted or unsubstituted ($C_1$–$C_6$)-alkyl, substituted or unsubstituted ($C_1$–$C_6$)-phenyl, and substituted or unsubstituted ($C_1$–$C_6$)-benzyl;
in the presence of a base or, if appropriate, of a dehydrating agent to give a compound of the formula IV:

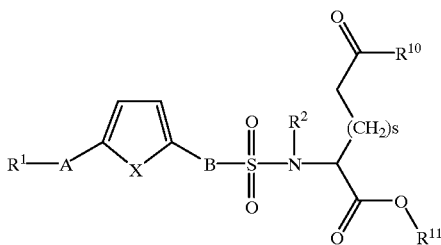

(IV)

by removing the protecting group $R^{12}$ and by introducing —N($R^6$)—$R^7$ by known peptide chemistry techniques, followed by removal of $R^{11}$, one may form a compound of formula I.

In another preferred embodiment, a compound of formula I can be prepared by a process comprising:

a) reacting an amino acid anhydride of the formula V:

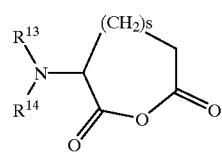

(V)

wherein, $R^{13}$ is hydrogen;
$R^{14}$ is an N-protecting group which includes carbobenzyloxy (Z); or
together $R^{13}$ and $R^{14}$ are a cyclic N-protecting group such as phthalimido,
with a primary or secondary radical —N($R^6$)—$R^7$ to open the anhydride ring to give an intermediate of the formula VI:

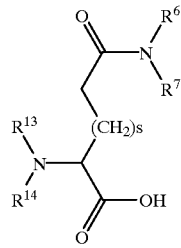

(VI)

This ring opening, depending on the protecting group and reaction conditions (cf., X. Huang, X. Luo, Y. Roupioz, J. W. Keillor, J. Org. Chem. 1997, 62, 8821–8825) as a rule regioselectively yields the isomer shown in formula VI, which, if regioisomer mixtures occur, can be further enriched by crystallization or chromatography. Cleaving the included protecting group ($R^{13}$, $R^{14}$ or both) with the release of the amine, followed by an N-sulfonation with a sulfonic acid derivative of the formula III as previously described leads to a product of the formula I.

In another embodiment of the invention, resolving a compound of the formula I prepared according to the processes of the invention which, on account of its chemical structure, occurs in enantiomeric forms may be accomplished. The resolution into the pure enantiomers may be performed by salt formation with enantiomerically pure acids or bases, chromatography on chiral stationary phases, or derivatization by means of chiral enantiomerically pure compounds such as amino acids. Separation of the diastereomers is thereby obtained. Removal of the chiral auxiliary groups, or isolating the compound of the formula I prepared according to the processes of the invention in free form or, if acidic or basic groups are present, converting it into physiologically tolerable salts may then be performed.

Suitable protecting groups for this are preferably the customary N-protecting groups used in peptide chemistry, for example protecting groups of the urethane type, benzyloxycarbonyl (Z), t-butyloxycarbonyl (Boc), 9-fluorenyloxycarbonyl (Fmoc), allyloxycarbonyl (Alloc) or of the acid amide type, in particular formyl, acetyl or trifluoroacetyl, and of the alkyl type, for example benzyl.

Starting materials used for the preparation of the sulfonic acid derivatives of the formula III are preferably sulfonic acids or their salts of the formula VII, for example

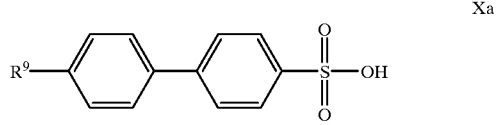

Xa

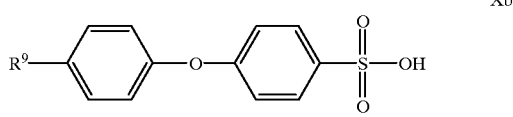

Xb

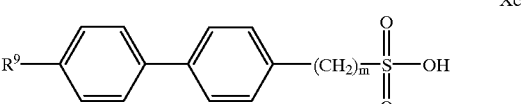

Xc

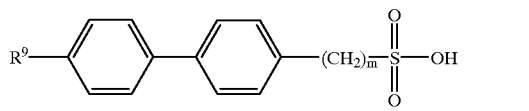

Xd

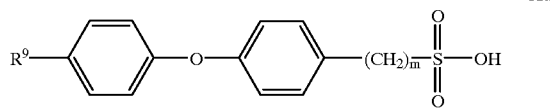

Xe

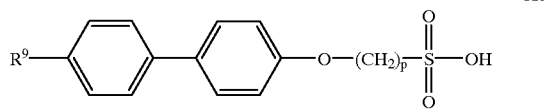

Xf

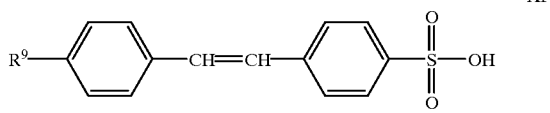

Xg

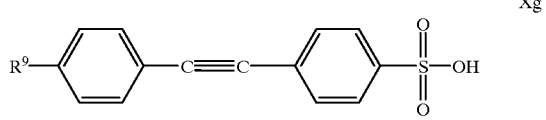

where $R^{15}$ has the same meaning as $R^1$.

Sulfonic acid derivatives of the formula III, which like $R^{15}$ contain a secondary or cyclic amine of the type —N($R^4$)—$R^5$, are prepared preferably and in high yields by Pd-catalyzed substitution of a bisaryl halide, preferably of a bromide, by a secondary amine following known literature procedures (cf. A. S. Guram, R. A. Rennels, S. L. Buchwald; Angew. Chem. 1995, 107, 1456–1459) and subsequent sulfochlorination by means of chlorosulfonic acid. The sulfochloride function is in this case preferably guided into the desired para position by the directing effect of the amine group.

The catalyst dichlorobis(tritolylphosphine)palladium(II) advantageously used can be prepared analogously to R. F.

Heck in "Palladium Reagents in Organic Syntheses", Academic Press, London (1985), p. 18 starting from tri-o-tolylphosphine, palladium(II) chloride and LiCl in methanol.

For the preparation of the arylsulfonic acids of the formulae VIIa and VIIb, the sulfonation process with concentrated sulfuric acid described in Houben-Weyl "Methoden der Organischen Chemie" [Methods of Organic Chemistry] volume 9, pp. 540–546 is preferably used, if appropriate in the presence of a catalyst, sulfur trioxide and its addition compounds or halosulfonic acids, such as chlorosulfonic acid. Particularly in the case of the diphenyl ethers of the formula VIIb, the use of concentrated sulfuric acid and acetic anhydride as a solvent (cf., C. M. Suter, J. Am. Chem. Soc. 53 (1931) 1114), or the reaction with excess chlorosulfonic acid (J. P. Bassin, R. Cremlyn and F. Swinbourne; Phosphorus, Sulfur and Silicon 72 (1992) 157) has proven suitable. Sulfonic acids according to the formulae VIIc, VIId, or VIIe can be prepared in a manner known per se by reacting the appropriate arylalkyl halide with sulfites such as sodium sulfite or ammonium sulfite in aqueous or aqueous/alcoholic solution, it being possible to accelerate the reaction in the presence of tetraorganoammonium salts such as tetrabutylammonium chloride.

Sulfonic acid derivatives according to formula III used, are, in particular, the sulfonyl chlorides. For their preparation, the corresponding sulfonic acids, also in the form of their salts such as sodium, ammonium or pyridinium salts, are reacted in a known manner with phosphorus pentachloride or thionyl chloride without or in the presence of a solvent such as phosphorus oxychloride or of an inert solvent such as methylene chloride, cyclohexane or chloroform, in general at reaction temperatures of 20° C. up to the boiling point of the reaction medium used. Advantageously, the direct sulfochlorination of the appropriate aromatic can also be carried out using chlorosulfonic acid, sulfuryl chloride or pyrosulfuryl chloride (Houben-Weyl, Methoden der Organischen Chemie [Methods of Organic Chemistry], volume 9 (1995), pages 572–579).

The reaction of the sulfonic acid derivatives of the formula III with the amino acids of the formula II according to process according to the invention proceeds advantageously in the style of the Schotten-Baumann reaction. Suitable bases for this are particularly alkali metal hydroxides such as sodium hydroxide, but also alkali metal acetates, alkali metal hydrogencarbonates, alkali metal carbonates and amines. The reaction takes place in water or in a water-miscible or nonmiscible solvent such as tetrahydrofuran (THF), acetone, dioxane or acetonitrile, the reaction temperature in general being kept from −10° C. to 50° C. In the case in which the reaction is carried out in anhydrous medium, tetrahydrofuran or methylene chloride, acetonitrile or dioxane in the presence of a base, such as triethylamine, N-methylmorpholine, N-ethyl- or diisopropylethylamine is especially used, optionally in the presence of N,N-dimethylaminopyridine as a catalyst.

In another variant, particularly when using polar starting materials which are present in unprotected form, the aminocarboxylic acids of the formula II can first be converted into their silylated form with the aid of a silylating agent such as bis-trimethylsilyl trifluoroacetamide (BSTFA) and they then react with sulfonic acid derivatives to give compounds of the formula IV.

The physiologically tolerable salts of the compounds of the formula I capable of salt formation, including their stereoisomeric forms, are readily prepared. With basic reagents such as hydroxides, carbonates, hydrogencarbonates, alkoxides and ammonia or organic bases, for example 2-amino-2-hydroxymethyl-1,3-propanediol (tromethamine), trimethyl- or triethylamine, ethanolamine or triethanolamine or alternatively basic amino acids, for example lysine, ornithine or arginine, the carboxylic acids form stable alkali metal, alkaline earth metal or, if appropriate, substituted ammonium salts. Salts of the compound of the formula I which are formed with the organic bases mentioned show a high water solubility. If the compounds of the formula I have basic groups, stable acid addition salts can also be prepared using strong acids. For this, both inorganic and organic acids such as hydrochloric, hydrobromic, sulfuric, phosphoric, methanesulfonic, benzenesulfonic, p-toluenesulfonic, 4-bromobenzenesulfonic, acetic, oxalic, tartaric, trifluoromethylsulfonic, cyclohexylamidosulfonic, succinic or trifluoroacetic acid are suitable.

The invention also relates to pharmaceuticals which contain an efficacious amount of at least one compound of the formula I, a physiologically tolerable salt thereof, and an optionally stereoisomeric form thereof, together with a pharmaceutically suitable and physiologically tolerable excipient, additive or other active compounds and auxiliaries.

On account of their pharmacological properties, the compounds according to the invention are suitable for the prophylaxis and therapy of all those disorders in whose course matrix-degrading metalloproteinases are involved. These include degenerative joint disorders such as osteoarthroses, rheumatoid arthritis, spondyloses, chondrolysis after joint trauma or relatively long immobilization of the joint, e.g. after meniscus or patella injuries or tearing of the ligaments. In addition, these also include disorders of the connective tissue such as collagenoses, periodontal disorders, which can even lead to the loss of the teeth, wound healing disorders and chronic disorders of the locomotory apparatus such as inflammatory, immunologically, or metabolically caused acute and chronic arthritis, arthropathies, myalgias, and disorders of the bone metabolism (such as osteoporosis). The medicinal use of the compounds of the formula I according to the invention may be indicated in the case of vascular diseases, e.g. blood vessel occlusions, atherosclerotic plaques or aneurysms, particularly in threatening rupture, or in stenoses of any pathogenesis. The compounds of the formula I are furthermore suitable for the treatment of inflammations, including wounds and ulcers, in particular also those of the skin, carcinomatous disorders, in particular also for blocking or checking the formation and spread of metastases, and also in carcinoma of the breast. Cachexia, anorexia, and septic shock and also periodontosis and periodontitis are further medicinal areas of application for the compounds according to the invention.

In general, the pharmaceuticals according to the invention are administered orally or parenterally. Rectal or transdermal administration is also possible.

The invention also relates to a process for the production of a pharmaceutical, which comprises bringing at least one compound of the formula I into a suitable administration form using a pharmaceutically suitable and physiologically tolerable vehicle, and, if appropriate, further suitable active compounds, additives or auxiliaries.

Suitable solid or pharmaceutical preparation forms are, for example, granules, powders, coated tablets, tablets, (micro)capsules, suppositories, syrups, juices, suspensions, emulsions, drops or injectable solutions as well as preparations with protracted release of active compound, in whose preparation customary auxiliaries, such as excipients, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactoprotein, gelatin, starch, cellulose and its derivatives, animal and vegetable oils such as cod-liver oil, sunflower oil, peanut or sesame oil, polyethylene glycol and solvents such as, for example, sterile water and mono- or polyhydric alcohols such as glycerol.

The pharmaceutical preparations are preferably prepared and administered in dose units, each unit containing as active constituent a specific dose of the compound of the formula I according to the invention. In the case of solid dose units such as tablets, capsules, coated tablets or suppositories, this dose can be up to approximately 1000 mg, but preferably approximately 50 to 300 mg and, in the case of injection solutions in ampoule form, up to approximately 300 mg, but preferably approximately 10 to 100 mg.

For the treatment of an adult patient weighing approximately 70 kg, depending on the efficacy of the compounds according to formula I, daily doses of approximately 20 mg to 1000 mg of active compound, preferably approximately 100 mg to 500 mg, are indicated. Under certain circumstances, however, even higher or lower daily doses may be appropriate. The daily dose can be administered both by single administration in the form of an individual dose unit or else of several smaller dose units and by multiple administration of subdivided doses at intervals.

The compounds on which the invention is based were identified by nuclear magnetic resonance and mass spectroscopy, where in the case of the presence of regio- or diastereoisomeric forms in addition to $^1$H also $^{13}$C and multidimensional NMR methods were employed for clear proof of structure. $^1$H NMR spectra have been recorded on a 400 MHz apparatus from Bruker, as a rule using tetramethylsilane (TMS) as an internal standard and at room temperature (RT). As a rule, final products are determined by mass spectroscopic methods (FAB-, ESI-MS with positive or negative ionization). Temperatures are in degrees Celsius, RT means room temperature (22° C. to 26° C.). Abbreviations used are either explained or correspond to the customary conventions.

PREPARATION EXAMPLES

Method (A)

Example 5

4-(3-(4-(Biphenyl-4-sulfonylamino)-4-carboxybutyrylamino)-propyl)morpholin-4-ium trifluoroacetate Stage 1: Sulfonation of glutamyl tert-butyl ester 3 g (0.0148 mol) of L-Glu-OtBu were dissolved in 29.5 ml of 0.5 N NaOH and 250 ml of tetrahydrofuran (THF) and cooled to 0° C. in an ice bath, and simultaneously (while keeping the pH constant at pH 8.5), a solution of 4.476 g (0.0177 mol) of biphenylsulfonyl chloride in 35 ml of THF and 29.52 ml of an aqueous 0.5 N NaOH was slowly added dropwise over approximately 30 minutes (min). After removing the ice bath, the mixture was stirred at room temperature for 3 hours (h) and the completion of the reaction was monitored by thin-layer chromatography (TLC). THF was removed under reduced pressure, the residue was extracted once with diethyl ether, the extract was acidified to pH 1.5 using 1 N HCl, the product was extracted a number of times with ethyl acetate, the extract was dried and the solvent was removed under reduced pressure. 2.89 g of product remained, which could be reacted further without further purification.

Stage 2: Conversion into the amide 0.25 g (0.596 mmol) of the product from stage 1 was dissolved in 50 ml of absolute THF, 0.119 g (0.63 mmol) of EDC (1-(3-dimethylaminopropyl)-3-ethylcarbodiimide hydrochloride) and 0.0845 g (0.55 mmol) of 1-hydroxybenzotriazole hydrate were added, the mixture was stirred for 30 min, then 0.268 ml (1.79 mmol) of N-(3-aminopropyl)morpholine was added carefully, and the mixture was stirred for approximately 8 h. It was taken up with water, acidified using 1 N HCl to pH 2, extracted a number of times with ethyl acetate, washed with dilute NaCl, dried and concentrated. Yield: 250 mg.

A further purification could be carried out by chromatography on silica gel by means of dichloromethane/methanol 9:1.

Stage 3: Removal of the protecting group 0.11 g of the product from stage 2 was dissolved in 5 ml of trifluoroacetic acid and 5 ml of dichloromethane and the mixture was stirred at room temperature for approximately 3 h under protecting gas until completion of the reaction (TLC checking). After concentration, the mixture was entrained a number of times with dichloromethane and the residue was dried under reduced pressure. 0.11 g of the compound of Example 5 remained as the trifluoroacetate.

Method (B)

Example 6

2-(Biphenyl-4-sulfonylamino)-5-(2,3-dihydroindol-1-yl)-5-oxo-pentanecarboxylic acid Stage 1: Reaction of phthaloyl-L-glutamyl anhydride with dihydroindole 1.5 g (0.0058 mol) of phthaloyl-L-glutamyl anhydride were dissolved in 15 ml absolute dioxane, and a solution of 0.813 ml (0.0073 mol) of dihydroindole in 15 ml of dioxane was added dropwise in the course of 10 min. The mixture was heated until the reaction was complete (approximately 5 h, TLC checking) at 40° C., concentrated, and the mixture was entrained a number of times under reduced pressure using dichloromethane.

Yield: 2.7 g (product contained approximately 15 mol % of dioxane).

Stage 2: Removal of the protecting group 2.43 g of the product from stage 1 were dissolved in 30 ml of ethanol and 0.39 ml (0.0080 mol) of hydrazine hydrate was added. The mixture was stirred at 80° C. for 3 h, concentrated to dryness under reduced pressure, the residue was taken up using 50 ml of 25% strength aqueous acetic acid and the mixture was heated at 80° C. for approximately 10 min. It was then cooled in an ice bath and the resulting precipitate was filtered off with suction, the precipitate was taken up again using acetic acid and this procedure was repeated. The phthalyl hydrazide residue which remained was discarded. The combined filtrates were concentrated, and afforded 0.7 g of product.

Stage 3: Introduction of the N-arylsulfonyl radical 0.5 g (0.002 mol) of the product from stage 2 was dissolved in 50 ml of THF/water (1:1) together with 0.45 g (0.0033 mol) of potassium carbonate, and a solution of 0.61 g (0.0024 mol) of biphenylsulfonyl chloride, dissolved in 50 ml of THF, was added dropwise in the course of 20 min. The mixture was stirred at RT until the reaction was complete (approximately 6 to 8 h, TLC checking), extracted once with diethyl ether and acidified to pH 1.5 using 1 N HCl, and the product was extracted a number of times with ethyl acetate, dried and concentrated under reduced pressure. After drying, 0.42 g of the product of Example 6 remained.

Method (C)

Example 8

2-(4'-Chlorobiphenyl-4-sulfonylamino)-5-(2,3-dihydroindol-1-yl)-5-oxopentanoic acid Stage 1: Reaction of Cbz-Glu anhydride with 2,3-dihydro-1H-indole 5 g (0.019 mol) of L-Cbz-glutamyl anhydride were dissolved in 100 ml of absolute dimethyl sulfoxide together with 2.56 ml (this corresponds to 0.023 mol) of 2,3-dihydro-1H-indole and the solution was stirred at room temperature (RT) for 30 min and at 40° C. for a further 30 min until the reaction was complete (TLC checking). The mixture was added to water, extracted with ethyl acetate a number of times, and the organic phase was washed with 1N HCl and with saturated NaCl solution, dried and concentrated.

Yield: 7.07 g.

Stage 2: Removal of the Cbz protecting group 6.8 g (0.018 mol) of the product from stage 1 were dissolved in 60 ml of a 33% strength HBr/glacial acetic acid solution in the course of 30 min and the solution was stirred at RT until the reaction was complete (about 15 h, TLC checking). The crude product obtained after concentration under reduced pressure was entrained a number of times with dichloromethane and taken up using methanol/water (10:1), and the product was filtered off, dried and again extracted by stirring in THF. After filtering off with suction and drying under reduced pressure, 2.13 g of the crystalline hydrobromide having a purity of 98% (according to HPLC) remained.

The reductive removal of the protecting group analogously to Example 12, stage 4, afforded the hydrochloride of 2-amino-5-(2,3-dihydroindol-1-yl)-5-oxopentanoic acid in 85% yield.

Stage 3: 2-(4'-Chlorobiphenyl-4-sulfonylamino)-5-(2,3-dihydroindol-1-yl)-5-oxopentanoic acid 0.33 g (1 mmol) of the product from stage 2 was dissolved in 60 ml of THF/water (1:1) and a pH of 12.0 was established using a titroprocessor and 0.5 N NaOH. Under constant pH, a solution of 0.345 g (1.2 mmol) of 4'-chlorobiphenyl-4-sulfonyl chloride, dissolved in 30 ml of THF, was added dropwise in the course of approximately 45 min. The mixture was stirred for a further 2 h at pH 12, (TLC checking), treated with 0.1 N HCl to pH 2, extracted a number of times with ethyl acetate, washed with water, dried and concentrated.

Yield: 0.395 g of melting point 182° C. and a purity of more than 92%. The 4-chlorobiphenylsulfonic acid detectable as a slight impurity could be removed by chromatography or reprecipitation.

Example 12

5-(5-Fluoro-2,3-dihydroindol-1-yl)-5-oxo-2-(4'-pyrrolidin-1-yl-biphenyl-4-sulfonylamino) pentanoic acid Stage 1: Biphenyl-4-ylpyrrolidine 10.0 g (0.043 mol) of 4-bromobiphenyl were suspended in 600 ml of toluene together with 3.7 g (0.052 mol) of pyrrolidine and 6.2 g (0.0642 mol) of sodium tertiary-butoxide and 900 mg of the catalyst dichlorobis(tritolylphosphine)palladium(ll) were added. The mixture was heated to reflux for 8 h, cooled, treated with water/ethyl acetate, and the organic phase was washed with water, dried over sodium sulfate and concentrated. The residue was dissolved in approximately 300 ml of tertiary-butyl methyl ether and the hydrochloride of the product was precipitated by addition of 50 ml of 1N ethereal HCl.

Yield: 6.0 g of melting point higher than 125° C. (decomposition).

Stage 2: 4'-Pyrrolidin-1-ylbiphenyl-4-sulfonyl chloride 6 g (0.023 mol) of the product from stage 1 was introduced into 11 ml of chlorosulfonic acid in portions with cooling and under protecting gas and the mixture was heated at 60° C. for 3.5 h. The solution was added to ice, the suspension was brought to pH 8 by addition of solid sodium bicarbonate, and the precipitated product was filtered off with suction and dried under reduced pressure.

Yield: 7 g of melting point higher than 282° C. (decomposition).

Stage 3: Reaction of Z-Glu anhydride with 5-fluro-2,3-dihydro-1H-indole 8.8 g (0.0334 mol) of L-Z-glutamyl anhydride were dissolved in 150 ml of absolute dimethyl sulfoxide together with 5.5 g (0.04 mol) of 5-fluoro-2,3-dihydro-1H-indole and the solution was stirred at RT until the reaction was complete (approximately 3 h, TLC checking). The mixture was added to water, extracted a number of times with ethyl acetate and the organic phase was washed with 1N HCl and with saturated NaCl, dried and concentrated.

Yield: 13.2 g.

Stage 4: Removal of the Z protecting group 13 g (0,0325 mol) of the product from stage 3 were dissolved in 450 ml of methanol and 33 ml of 1N HCl, a spatula tipful of palladium on carbon was added, and the mixture was hydrogenated at 40 bar and 60° C. until the reaction was complete (TLC checking). The crude product obtained after filtration and concentration was taken up in THF under reflux, and the solid hydrochloride which remained after cooling was filtered off and dried under reduced pressure.

Yield: 7.1 g of melting point higher than 212° C.

Stage 5: 5-(5-Fluoro-2,3-dihydroindol-1-yl)-5-oxo-2-(4'-pyrrolidin-1-ylbiphenyl-4-sulfonylamino) pentanoic acid 0.303 g (1 mmol) of the product from stage 4 was dissolved in 60 ml of THF/water (1:1) and a pH of 12.0 was established using a titroprocessor (model 686, Metrohm) by means of 0.5 N NaOH. While keeping the pH constant, a solution of 0.39 g (1.2 mmol) of the product from stage 2, dissolved in 40 ml of THF, was added dropwise in the course of approximately 45 min. The mixture was stirred for a further 2 h at pH 12 (TLC checking), treated with 0.1 N HCl until a pH of 2 was achieved and extracted a number of times with ethyl acetate, and the extract was washed with water, dried and concentrated. The product was purified by chromatography on silica gel (dichloromethane/methanol 95:5).

Yield: 0.393 g of melting point 216° C.

Method (D)

Example 15

Tromethamine salt of 2-(4'-chlorobiphenyl-4-sulfonylamino)-5-(2,3-dihydroindol-1-yl)-5-oxopentanoic acid 104.5 g (0.21 mol) of the compound according to Example 8 were suspended in 1000 ml of ethanol and warmed to 50° C. 25.4 g of tromethamine (2-amino-2-hydroxymethyl-1,3-propanediol, TRIS) dissolved in 100 ml of water were then added thereto. The mixture was briefly heated to reflux and filtered hot. The clear filtrate was allowed to cool to RT, whereupon the salt precipitated. It was filtered off with suction and washed twice with 150 ml of ethanol/water in a ratio of 9 to 1 each time and dried in a desiccator.

Yield: 93.9 g (72%) of tromethamine salt.

Example 16

Tris-(2-hydroxyethyl)ammonium 2-(4'-chlorobiphenyl-4-sulfonylamino)-5-(2,3-dihydroindol-1-yl)-5-oxopentanoate 0.05 g of the product from Example 8 was dissolved in 3.18 g of acetone, 0.01 g of triethanolamine was added, and the solution was filtered and placed in an open Erlenmeyer vessel in a TLC chamber whose bottom was covered to approximately 1 cm with tert-butyl methyl ether. Crystal formation commenced after approximately 10 h and was complete after 4 to 5 days. The supernatant solvent was decanted off and the product obtained was dried under reduced pressure.

Yield: 0.06 g of melting point 120° C.

Examples 1 to 5 of Table 1 were prepared according to method (A), Examples 6 and 7 according to method (B) and Examples 8 to 14 according to method (C). The starting material needed for the introduction of the arylsulfonyl side chain of Example 13 (4'-morpholin-4-ylbiphenyl-4-sulfonyl chloride) was prepared analogously to method (C), stage 1.

TABLE 1

| Example | Structure | Comment | Molecular weight | Melting point (° C.) | MS (M − H) |
|---|---|---|---|---|---|
| 1 | 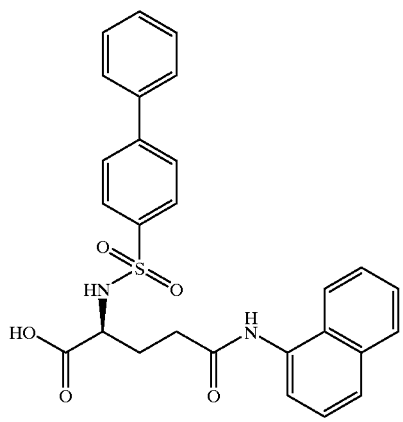 | S-isomer | 488.56 | 203 | 489.3 (M + H) |
| 2 | 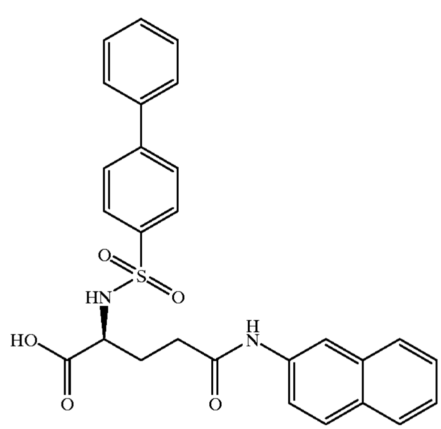 | S-isomer | 488.56 | 249.5 | 487.3 |

TABLE 1-continued

| Example | Structure | Comment | Molecular weight | Melting point (° C.) | MS (M − H) |
|---|---|---|---|---|---|
| 3 | 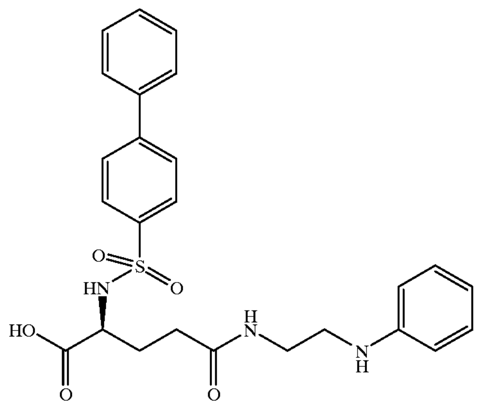 | S-isomer | 481.57 | 120 | 482.2 (M + 1) |
| 4 | 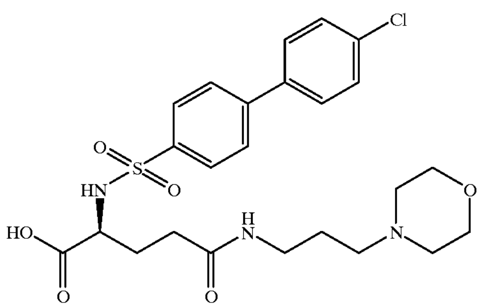 | S-isomer | 524.01 | 170 (decomposition) | 524.4/ 526.4 |
| 5 | 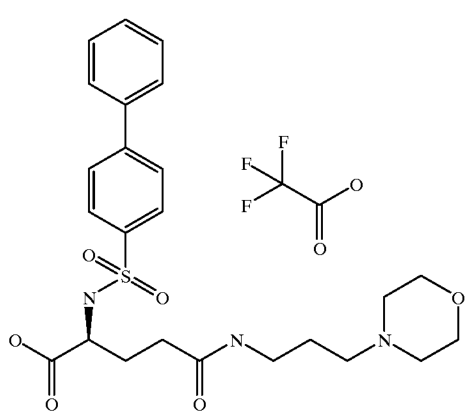 | S-isomer | 603.61 | 102 | 490.3 (M + 1) |

TABLE 1-continued

| Example | Structure | Comment | Molecular weight | Melting point (° C.) | MS (M − H) |
|---|---|---|---|---|---|
| 6 | Chiral | S-isomer | 464.54 | 183 | 462.9 |
| 7 | Chiral | S-isomer | 533.65 | 130 (decomposition) | 532.3 |
| 8 | Chiral | S-isomer | 498.98 | 182 | 497.0 |

TABLE 1-continued

| Example | Structure | Comment | Molecular weight | Melting point (° C.) | MS (M − H) |
|---|---|---|---|---|---|
| 9 | Chiral, 4'-Br-biphenyl-sulfonamide glutamic acid indoline amide | S-isomer | 543.44 | 187 | 541.0/543.0 |
| 10 | Chiral, 4'-Cl-biphenyl-sulfonamide glutamic acid 5-fluoroindoline amide | S-isomer | 516.97 | 190 (decomposition) | 515.0 |
| 11 | Chiral, 4'-Br-biphenyl-sulfonamide glutamic acid 5-fluoroindoline amide | S-isomer | 561.43 | 194 | 559.0/561.0 |

TABLE 1-continued
| Example | Structure | Comment | Molecular weight | Melting point (° C.) | MS (M − H) |
|---|---|---|---|---|---|
| 12 | 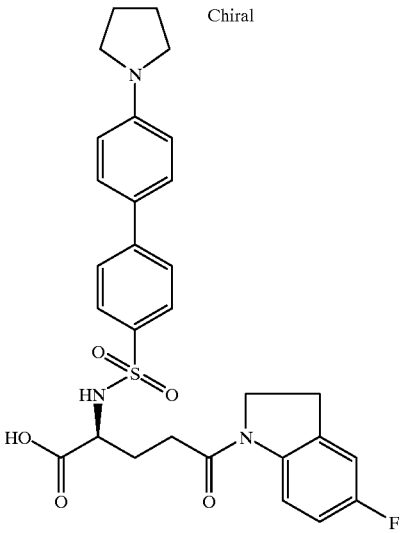 Chiral | S-isomer | 551.64 | 216 | 550.0 |
| 13 | 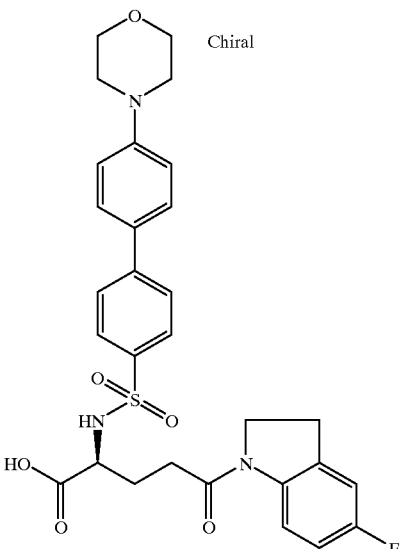 Chiral | S-isomer | 567.64 | 215 (decomposition) | 566.0 |

TABLE 1-continued

| Example | Structure | Comment | Molecular weight | Melting point (° C.) | MS (M − H) |
|---|---|---|---|---|---|
| 14 | 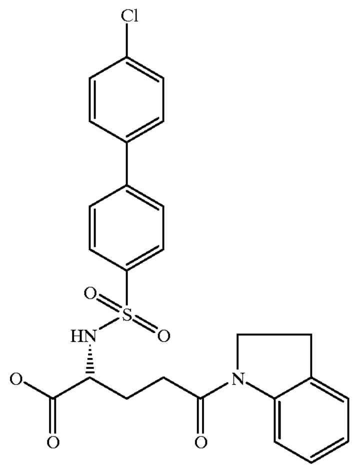 | R-isomer | 498.98 | 182 | 497.0 |

PHARMACOLOGICAL EXAMPLES

Preparation and determination of the enzymatic activity of the catalytic domain of human stromelysin and of neutrophil collagenase.

The two enzymes—stromelysin (MMP-3) and neutrophil collagenase (MMP-8)—were prepared according to Ye et al. (Biochemistry; 31 (1992) pages 11231–11235) or Weithmann et al. (Inflamm Res 46(1997) 246–252). For measurement of the inhibitory action on the enzymatic activity, 70 μl of buffer solution and 10 μl of enzyme solution were incubated for 15 minutes with 10 μl of a 10% strength (v/v) aqueous dimethyl sulfoxide solution which optionally contained the enzyme inhibitor. After addition of 10 μl of a 10% trength (v/v) aqueous dimethyl sulfoxide solution which contained 1 mmol/l of the substrate, the enzyme reaction was monitored by fluorescence spectroscopy (328 nm (ex)/ 393 nm (em)). The enzyme activity was shown as the extinction increase/minute. The $IC_{50}$ values listed in table 2 were determined as those inhibitor concentrations which in each case led to a 50% inhibition of the enzyme. The buffer solution contained 0.05% of Brij (Sigma, Deisenhofen, Germany) and 0.1 mol/l of piperazine-N,N'-bis[2-ethanesulfonic acid]/NaOH, 0.1 mol/l of NaCl, 0.01 mol/l of $CaCl_2$ and 0.1 mol/l of piperazine-N,N'-bis[2-ethanesulfonic acid] (pH=6.5). The enezyme solution contained 5 μg/ml of one of the enzyme domains prepared according to Ye et al. The substrate solution contained 1 mmol/l of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-$NH_2$ (Bachem, Heidelberg, Germany).

TABLE 2

| Example | MMP-3 $IC_{50}$ [μmol/l] | MMP-8 $IC_{50}$ [μmol/l] |
|---|---|---|
| 1 | 0.1 | 0.01 |
| 2 | 0.2 | 0.02 |
| 3 | 0.2 | 0.02 |
| 4 | 0.1 | 0.02 |
| 5 | 0.1 | 0.006 |
| 6 | 0.5 | 0.02 |
| 7 | 0.04 | 0.004 |
| 8 | 0.1 | 0.01 |
| 9 | 0.1 | 0.02 |
| 10 | 0.1 | 0.02 |
| 11 | 0.1 | 0.02 |
| 12 | 0.03 | 0.002 |
| 13 | 0.1 | 0.01 |
| 14 | 0.05 | 0.01 |

Determination of the solubility in water of the free acid of 2-(4'-chloro-biphenyl-4-sulfonylamino)-5-(5-fluoro-2,3-dihydroindol-1-yl)-5-oxo-pentanoic acid according to Example 8 and its tromethamine salt according to Example 15

1. Materials Employed
1.1 Test substances
   a) Compound according to Example 8; 2-(4'-chlorobiphenyl-4-sulfonylamino)-5-(5-fluoro-2,3-dihydroindol-1-yl)-5-oxopentanoic acid
   b) Compound according to Example 15; tromethamine salt of 2-(4'-chlorobiphenyl-4-sulfonylamino)-5-(5-fluoro-2,3-dihydroindol-1-yl)-5-oxopentanoic acid
1.2 Reagents
   Water: deionized, Acetonitrile: LiChrosolv (Merck),
   Diethylamine: for synthesis (Merck), Acetic acid: concentrated and 1N (Merck)
2. Experimental Procedure
2.1 2-(4'-Chlorobiphenyl-4-sulfonylamino)-5-(5-fluoro-2,3-dihydroindol-1-yl)-5-oxopentanoic acid Approximately 50 mg of test substance according to 1.1a) were initially introduced into a 100 ml Erlenmeyer flask. After addition of 10 ml of water, the mixture was stirred at 25° C. After 2 hours (h) and after 3 h, aliquots were taken and centrifuged. 1 ml each of the supernatant was diluted to 10 ml with mobile phase. The concentration of the active component was determined by means of HPLC against an external standard. Repetition of the experiment.

2.2 Tromethamine salt of 2-(4'-chlorobiphenyl-4-sulfonylamino)-5-(5-fluoro-2,3-dihydroindol-1-yl)-5-oxopentanoic acid Approximately 800 mg of the tromethamine salt according to 1.1 b) were initially introduced into a 100 ml Erlenmeyer flask. After addition of 10 ml of water, the mixture was stirred at 25° C. After 2 h and after 3 h, aliquots were taken and centrifuged. 1 ml each of the supernatant was diluted to 100 ml with mobile phase. The concentration of the active component was determined by means of HPLC against an external standard. Repetition of the experiment.

| 3. Analysis | |
|---|---|
| Instrument: | Gynkotek HPLC unit |
| Column: | Stationary phase: ChiraDex 5 μm, Merck Dimensions: 250 mm × 4.0 mm |
| Mobile phase: | Acetonitrile 440 ml; water 560 ml; diethylamine 1 ml; adjusted to pH 6.4 using acetic acid. |
| Injection volume: | 10 μml |
| Flow: | 0.8 ml/min |
| Column temperature: | 40° C. |
| Detection: | UV at 261 nm |

| 5. Results | | | |
|---|---|---|---|
| | Solubility in water at 25° C. (mg/ml) | | |
| | after 2 h* | After 3 h* | Result |
| 2-(4'-Chlorobiphenyl-4-sulfonyl-amino)-5-(5-fluoro-2,3-dihydroindol-1-yl)-5-oxopentanoic acid | 0.2 | 0.1 | 0.1 |
| Tromethamine salt of 2-(4'-chloro-biphenyl-4-sulfonylamino)-5-(5-fluoro-2,3-dihydroindol-1-yl)-5-oxopentanoic acid | 58 | 58 | 58 |

*Mean value from two determinations

The time-dependent difference in the solubility values of 2-(4'-chlorobiphenyl-4-sulfonylamino)-5-(5-fluoro-2,3-dihydroindol-1-yl)-5-oxopentanoic acid could be attributable to supersaturation/saturation phenomena. As a result, the data value obtained after 3 h is used.

The water solubility of the tromethamine salt of 2-(4'-chlorobiphenyl-4-sulfonylamino)-5-(5-fluoro-2,3-dihydroindol-1-yl)-5-oxopentanoic acid is higher approximately by a factor of 600 than that of the free acid of 2-(4'-chlorobiphenyl-4-sulfonylamino)-5-(5-fluoro-2,3-dihydroindol-1-yl)-5-oxopentanoic acid.

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

We claim:

1. A compound of the formula I or a stereoisomer or a pharmaceutically acceptable salt of the foregoing:

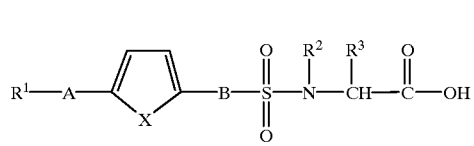

wherein, $R^1$ is phenyl monosubstituted by a 5 membered-ring containing 1 or 2 nitrogen atoms;

$R^2$ is selected from
1) hydrogen,
2) linear $(C_1-C_6)$-alkyl, and
3) phenyl;

$R^3$ is $-(C_1-C_4)$-alkyl-$C(O)-N(R^6)-R^7$;

where $R^6$ and $R^7$ together with the nitrogen to which they are bonded form a radical of formula IIa:

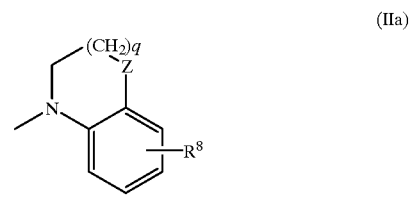

wherein
q is zero;
Z is carbon;

$R^8$ is selected from
1) hydrogen
2) linear $(C_1-C_6)$-alkyl,
3) branched $(C_1-C_6)$-alkyl,
4) cyclic $(C_3-C_6)$-alkyl,
5) hydroxyl,
6) $(C_1-C_6)$-alkyl-$C(O)-O-$,
7) $(C_1-C_6)$-alkyl-$O-$,
8) $(C_1-C_6)$-alkyl-$O-(C_1-C_4)$-alkyl-$O-$,
9) halogen,
10) $CF_3$,
11) CN,
12) $NO_2$
13) HO—$C(O)-$,
14) $(C_1-C_6)$-alkyl-$O-C(O)-$,
15) methylenedioxo,
16) $R^4-(R^5)N-C(O)-$, and
17) $R^4-(R^5)N-$;

A is a covalent bond;

B is $-(CH_2)_m-$,
where m is selected from zero, 1, 2, 3, 4, 5, and 6;

X is $-CH=CH-$;

$R^4$ and $R^5$ are independently selected from
1) hydrogen,
2) $(C_1-C_6)$-alkyl,
3) HO—$C(O)-(C_1-C_6)$-alkyl,
4) picolyl, 5) phenyl-$(CH_2)_n$—, where phenyl is unsubstituted, monosubstituted, or disubstituted with at least one substituent selected from linear $(C_1-C_6)$-alkyl, branched $(C_1-C_6)$-alkyl, cyclic $(C_3-C_6)$-alkyl, hydroxyl, $(C_1-C_6)$-alkyl-C(O)—O—, $(C_1-C_6)$-alkyl-O—, $(C_1-C_6)$-alkyl-O—$(C_1-C_4)$-alkyl-O, halogen, $CF_3$, CN, $NO_2$, HO—C(O)—, $(C_1-C_6)$-alkyl-O—C(O), methylenedioxo, $R^{4a}$—$(R^{5a})$N—C(O), and $R^{4a}$—$(R^{5a})$N—;

where $R^{4a}$ and $R^{5a}$ are independently selected from hydrogen, $(C_1-C_6)$-alkyl, HO—C(O)—$(C_1-C_6)$-alkyl, substituted or unsubstituted phenyl-$(CH_2)_n$—, and picolyl;

n is selected from zero, 1, and 2;

or together $R^4$ and $R^5$, form a 4, 5, 6, or 7 membered ring with the nitrogen to which $R^4$ and $R^5$ are attached wherein the remaining ring atoms are carbon.

2. The compound according to claim 1 of formula 1, wherein $R^2$ is selected from hydrogen and linear $(C_1-C_6)$ alkyl; and $R^4$ and $R^5$ are independently selected from hydrogen and $(C_1-C_6)$-alkyl or $R^4$ and $R^5$ together form a 4, 5, 6, or 7 membered ring with the nitrogen to which $R^4$ and $R^5$ are attached, wherein the remaining ring atoms are carbon.

3. The compound according to claim 2 of formula 1, wherein $R^2$ is hydrogen; and $R^8$ is selected from hydrogen, chlorine, bromine, and fluorine.

4. The compound according to claim 1 of formula I selected from 5-(2,3-) dihydroindol-1-yl)-5-oxo-2-(4'-pyrrolidin-1-yl-biphenyl-4-sulfonylamino)pentanoic acid and 5-(5-fluoro-2,3-dihydroindol-1-yl)-5-oxo-2-(4'-pyrrolidin-1-yl-biphenyl-4-sulfonylamino) pentanoic acid.

5. The compound according to claim 4, which is a salt selected from a 2-amino-2-) hydroxymethyl-1,3-propanediol salt, a trimethylamine salt, a triethylamine salt, an ethanolamine salt, and a triethanolamine salt.

6. A process for the producing a pharmaceutical, comprising combining at least one compound of the formula I as claimed in claim 4 with a pharmaceutically suitable and physiologically tolerable vehicle to form a pharmaceutically suitable administration form.

* * * * *

UNITED STATES PATENT AND TRADEMARK OFFICE
CERTIFICATE OF CORRECTION

PATENT NO.    : 6,201,130 B1
DATED         : March 13, 2001
INVENTOR(S)   : Wilfried Schwab et al.

It is certified that error appears in the above-identified patent and that said Letters Patent is hereby corrected as shown below:

<u>Title page,</u>
Item [73], in the Assignee, line 1, "Duetschland" should read -- Deutschland --.

<u>Column 29, claim 2,</u>
Line 18, "formula 1" should read -- formula I --.

<u>Column 30, claim 3,</u>
Line 3, "formula 1" should read -- formula I --.

<u>Column 30, claim 4,</u>
Line 10, "5-(2,3-)" should read -- 5-(2,3- --.

<u>Column 30, claim 5,</u>
Line 16, "2-amino-2-)" should read -- 2-amino-2- --.

Signed and Sealed this

Second Day of April, 2002

Attest:

Attesting Officer

JAMES E. ROGAN
Director of the United States Patent and Trademark Office